United States Patent [19]
Nguyen

[11] Patent Number: 5,840,219
[45] Date of Patent: Nov. 24, 1998

[54] INTRAOCULAR LENSES AND METHODS FOR MAKING SAME

[75] Inventor: Tuan A. Nguyen, Fountain Valley, Calif.

[73] Assignee: Allergan, Waco, Tex.

[21] Appl. No.: 858,549

[22] Filed: May 19, 1997

Related U.S. Application Data

[62] Division of Ser. No. 603,510, Feb. 20, 1996, Pat. No. 5,725,574, which is a continuation of Ser. No. 315,736, Sep. 30, 1994, abandoned, which is a continuation of Ser. No. 126,728, Sep. 24, 1993, abandoned, which is a continuation of Ser. No. 933,410, Aug. 21, 1992, abandoned.

[51] Int. Cl.$^6$ ....................................................... B29D 11/00
[52] U.S. Cl. ............................... 264/2.7; 264/1.1; 264/1.7
[58] Field of Search ............................... 264/1.1, 1.7, 2.7; 623/6

[56] References Cited

U.S. PATENT DOCUMENTS

| | | |
|---|---|---|
| 3,470,291 | 9/1969 | Johnson . |
| 3,632,841 | 1/1972 | Fortin . |
| 4,174,543 | 11/1979 | Kelman . |
| 4,310,485 | 1/1982 | Dauber . |
| 4,360,483 | 11/1982 | Ayres . |
| 4,454,203 | 6/1984 | Franz et al. . |
| 4,476,591 | 10/1984 | Arnott . |
| 4,550,057 | 10/1985 | Kataoka . |
| 4,676,791 | 6/1987 | Lemaster et al. . |
| 4,687,485 | 8/1987 | Lim et al. . |
| 4,725,397 | 2/1988 | Nakauchi et al. . |
| 4,774,036 | 9/1988 | Lemaster et al. . |
| 4,781,717 | 11/1988 | Grendahl . |
| 4,813,954 | 3/1989 | Siepser . |
| 4,813,956 | 3/1989 | Gupta . |
| 4,834,750 | 5/1989 | Gupta . |
| 4,919,662 | 4/1990 | Knoll et al. . |
| 4,932,968 | 6/1990 | Caldwell et al. . |
| 4,993,936 | 2/1991 | Siepser . |
| 4,995,879 | 2/1991 | Dougherty . |
| 5,120,120 | 6/1992 | Cohen . |
| 5,169,569 | 12/1992 | Ingram et al. . |
| 5,322,649 | 6/1994 | Rheinish et al. . |

FOREIGN PATENT DOCUMENTS

| | | |
|---|---|---|
| 0438043 | 7/1991 | European Pat. Off. . |
| 0444951 | 9/1991 | European Pat. Off. . |
| 2673574 | 9/1992 | France . |
| 2181355 | 4/1987 | United Kingdom . |

OTHER PUBLICATIONS

Encyclopedia of Polymer Science and Engineering, J. Wiley & Sons, vol. 10, pp. 613–616, 1988.

*Primary Examiner*—Mathieu D. Vargot
*Attorney, Agent, or Firm*—Frank J. Uxa

[57] ABSTRACT

New intraocular lenses and methods for producing such lenses are included. In one embodiment, the intraocular lens includes an optic; and at least one fixation member, e.g., haptic, secured to and extending from the optic, the fixation member being made from a compressed item having a compressed thickness and made of a polymer selected from the group consisting of methyl methacrylate homopolymers, methyl methacrylate-containing copolymers and mixtures thereof, the compressed item being derived by subjecting an item having a thickness to compression, preferably along an axis substantially parallel to the thickness, to reduce the thickness, provided that the compressed item has increased tensile strength relative to the item and is substantially no less intraocular lens manufacturable than is the item.

18 Claims, 1 Drawing Sheet

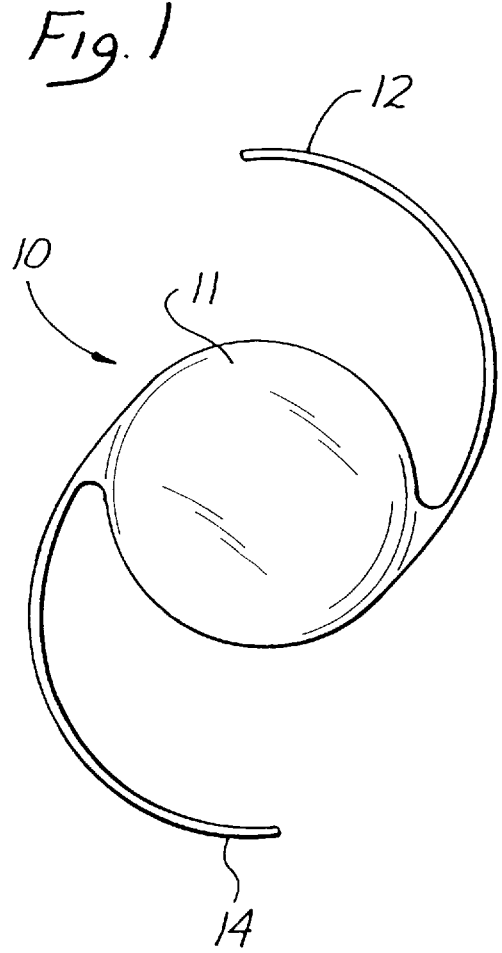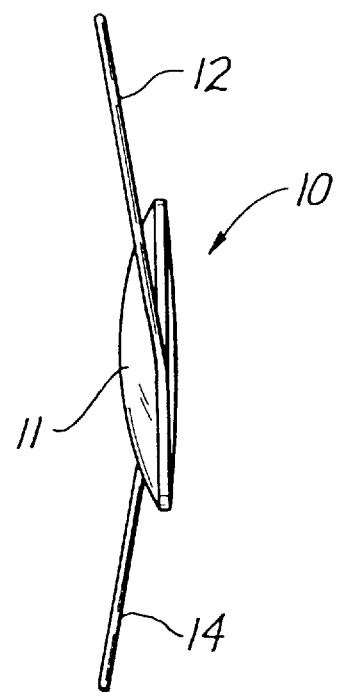

5,840,219

1

INTRAOCULAR LENSES AND METHODS FOR MAKING SAME

This is a division of application Ser. No. 08/603,510 filed Feb. 20, 1996, now U.S. Pat. No. 5,725,574; which is a continuation of application Ser. No. 08/315,736 filed Sep. 30, 1994 and now abandoned; which is a continuation of application Ser. No. 08/126,728 filed Sep. 24, 1993 and now abandoned; which is a continuation of application Ser. No. 07/933,410 filed Aug. 21, 1992 and now abandoned.

BACKGROUND OF THE INVENTION

The present invention relates to intraocular lenses and to methods for making such lenses. More particularly, the present invention relates to intraocular lenses having one or more enhanced physical properties, for example, tensile strength and/or flexibility, which benefit the lenses.

The use of intraocular lenses (IOLs) to improve vision and/or to replace damaged or diseased natural lenses in human eyes, particularly natural lenses impaired by cataracts, has achieved wide acceptance. Accordingly, a variety of IOLs has been developed for surgical implantation in the posterior or anterior chambers of the eye according to a patient's needs.

Known IOLs comprise an optical lens portion or optic which includes an optical zone, and one or more, preferably two, supporting structures, called fixation members or haptics, which are secured to and extend from the optic and are for contacting eye tissue to fix or hold the IOL in the proper position after implantation. The optic and the fixation member or members may each comprise a material such as a homopolymer of methyl methacrylate or polymethylmethacrylate (PMMA) or a copolymer containing methyl methacrylate. The entire IOL, that is the optic and the fixation member or members, may be made of a single piece or item of material, for example, PMMA.

In order to obtain a high degree of performance, the IOL should be made of a material or materials which have good physical or mechanical properties. For example, the fixation member or members should have sufficient tensile strength, flexibility and fatigue resistance so as not to break or separate from the optic during IOL implantation and to be effective in long term use in the eye. Certain materials, in particular, the methyl methacrylate-containing polymers noted above, have certain properties, such as optical clarity and biocompatibility, which make them very useful in IOLs. However, it would be advantageous to enhance certain other physical properties, as noted above, of such materials to further benefit IOLs made at least in part from such materials. This physical property enhancement would be all the more beneficial if it could be accomplished without the need for any substantial or significant change or changes (other than the enhancement itself) in the manner in which IOLs are produced.

European Patent Publication No. 0438043A2 discloses IOLs made from PMMA which is subjected to stretching along at least two mutually angulated axes to increase the material's dimension along the axes of stretch by 20% to 65%, preferably by 40%, thereby providing increased tensile strength and flexibility. Several disadvantages are apparent with such a "multi-axial" stretching system. For example, the material may not be uniformly stretched, which can cause distortions and other irregularities in the material and the final IOL product. In addition, because a relatively complex and cumbersome clamping/stretching system is employed, a relatively high percentage of the stretched material must be discarded. Further, the amount or degree of stretching is quite high, apparently because of the relative inefficiency of the "multi-axial" stretching technique in providing improved mechanical properties. Materials which are highly stretched have a tendency to be more difficult, relative to unstretched materials, to manufacture, for example, machine, into IOLs.

Kataoka U.S. Pat. No. 4,550,057 discloses compressing PMMA sheets to reduce the thickness of the sheet by a factor of at least 3 and increase impact resistance by a factor of at least 10. Large compression forces and/or temperatures on the order of 130° C. to 160° C. are employed to achieve this large degree of compression. These compressed sheets are suitable as a glazing material for windows for vehicles and buildings. This patent does not in any way disclose or suggest anything about IOLs or making IOLs.

Fortin U.S. Pat. No. 3,632,841 discloses compression stretching large acrylic sheets at temperatures of 250° F. and above between polished, heated and lubricated plates to form compressed sheets which are about one-third as thick as the original sheets. This patent discloses that such compression stretching provides improved physical and optical properties. This patent does not in any way disclose or suggest anything about IOLs or making IOLs.

Franz et al U.S. Pat. No. 4,454,203 discloses coating an acrylic substrate with a compatible polymeric film which is less extensible than the substrate and pressing the coated article to reduce thickness so that the compressed article has a thickness of about one-third that of the original article. Reduced amounts of compressive force are apparently required to achieve this large reduction in thickness, and the resulting plastic article is said to have improved optical quality. This patent does not in any way disclose or suggest anything about IOLs or making IOLs.

There continues to be a need for IOLs having enhanced properties and for methods for making such IOLs.

SUMMARY OF THE INVENTION

New IOLs and methods for producing IOLs have been discovered. The present IOLs are derived from materials containing methyl methacrylate-containing polymers which have been subjected to controlled and limited compression to enhance one or more physical properties of the materials and the resulting IOLs. It has been found that meaningful physical property enhancement can be achieved without substantially interfering with the overall IOL manufacturing process. For example, the limited compression to which the materials are subjected in accordance with the present invention provide enhanced tensile strength, flexibility and/or fatigue resistance, without forming a material which is substantially more difficult to manufacture into an IOL. Thus, after being compressed, the "compressed" material may be processed, for example, in accordance with conventional IOL manufacturing procedures, to obtain an IOL having advantageously enhanced physical properties. Because the present compression processing involves a more uniform application of force without clamping the material being processed, less material is wasted and/or a more uniform IOL is produced, for example, relative to the "multi-axial" stretching process of the prior art.

In one broad aspect, the present invention involves IOLs which comprise an optic and at least one fixation member which is secured to and extends from the optic. The fixation member or members, and preferably the optic as well, are made from a compressed item having a compressed thickness and comprising a polymer selected from methyl methacrylate homopolymers, methyl methacrylate-containing copolymers and mixtures thereof. The compressed item is derived by subjecting an item to compression, preferably along an axis substantially parallel to the thickness of the item, to reduce this thickness. The tensile strength of the compressed item is increased relative to the tensile strength of the item prior to being compressed. In one embodiment, the compression is preferably controlled so that the compressed item is substantially no less IOL manufacturable than the original, uncompressed item. That is, the compressed item can preferably be manufactured into an IOL substantially as easily, for example, using substantially no more energy, time, cost and/or effort, as can the original, uncompressed item be manufactured into an IOL.

In a particularly useful embodiment, the thickness of the uncompressed item is reduced by 30% or less as a result of the compression. In other words, the compressed thickness of the compressed item is equal to 70% or more of the thickness of the original, uncompressed item. This feature, which is one indication of the controlled or limited amount of compression involved in the present invention, provides meaningful enhancements in one or more of the physical properties of the item, and the IOL derived therefrom, and clearly distinguishes the present invention from the prior art. Thus, previous compression processing of PMMA and similar materials have involved substantially greater thickness reductions. The present invention is based, in part, on the discovery that sufficient enhancements in material physical properties can be achieved to benefit IOLs with a controlled or limited amount of compression. An additional benefit of this controlled, limited amount of compression is that the compressed material is substantially free of distortions and non-uniformities which become more prevalent as the degree of compression or stretching to which an item is subjected is increased.

In a further embodiment, the item is preferably subjected to compression at a temperature in the range of about 80° C. to about 130° C., more preferably about 80° C. to about 125° C. These relatively mild temperatures are consistent or in line with the controlled or limited degree of compression to which the item is subjected in accordance with the present invention. The mild temperatures noted herein reduce the amount of time involved in processing, for example, in heating and cooling, the material in accordance with the present invention. In addition, these mild temperatures reduce, or even eliminate, any distortions or non-uniformities which can result in processing the present materials at higher temperatures where the materials are more flowable and subject to change. Further, such mild temperatures reduce, or even eliminate, depolymerization of the present materials so that longer polymer chains are maintained and compressed materials having one or more superior physical properties are obtained, relative to processing at higher temperatures.

In one embodiment, only the fixation member or members of the IOL are produced from a compressed item in accordance with the present invention. Alternately, the optic and fixation member or members of the IOL are produced from the compressed item of material. In a useful embodiment, a single IOL is formed from the compressed item. This feature again distinguishes the present invention from the prior art which discloses stretching or compressing large sheets of PMMA and the like materials. However, it should be noted that two, three, four or more IOLs can be produced from a single compressed item.

In another aspect of the present invention, methods for making IOLs are provided. These methods comprise compressing an item having a thickness, preferably along an axis substantially parallel to the thickness, to reduce the thickness and form a compressed item. The item comprises a polymer selected from methyl methacrylate homopolymers, methyl methacrylate-containing copolymers and mixtures thereof. This compressed item has increased tensile strength relative to the original, uncompressed item. An IOL is formed from the compressed item and includes an optic and at least one fixation member secured to the optic and extending from the optic. In a particularly useful embodiment, the forming step includes machining the compressed item and the compressing occurs at conditions such that the machining is substantially no more difficult, for example, relative to substantially identically machining the original, uncompressed item.

The present IOLs have enhanced physical properties which reduce the risk of disassembly or degradation during installation or long term use in the eye. Such physical property enhancement is achieved with little or no detriment, for example, to the conventional IOL manufacturing process. Further, the present methods for producing IOLs involve controlled or limited amounts of compression so as to reduce, and even minimize, material waste, energy and processing inefficiencies, and distortions and non-uniformities in the final IOL products. The present invention very efficiently and effectively provides IOLs which have enhanced physical properties and are advantageously useful and durable.

BRIEF DESCRIPTION OF THE DRAWINGS

FIG. 1 is a front view of a typical IOL including optic and fixation members made of a material embodying principles of the present invention.

FIG. 2 is a side view of the lens of FIG. 1.

DETAILED DESCRIPTION OF THE INVENTION

Many different IOL configurations and sizes may be employed in the present invention. To illustrate, a typical IOL is shown generally at 10 in FIG. 1, and includes an optic 11 suitably shaped for proper focusing and having integrally formed fixation members or haptics 12 and 14 extending therefrom. IOL 10 may be. plano-convex, as shown, or bi-convex, concavo-convex or any other optical configuration as desired. The optic may also have refractive and diffractive optic portions, several refractive curves or an aspheric surface to give bifocal or multifocal capabilities and be formed of a material having different optical or physical properties than the material forming haptics 12 and 14. Any haptic shape, configuration, or number may be utilized in accordance with the teachings of the present invention. Small apertures, notches and the like may be provided in the optic 11, for example, adjacent the connection with haptics 12 and 14, respectively, for reception of implantation tools.

In lenses of this type, the central portion or optic is a solid body, for example, about 5 mm to about 8 mm in diameter, with the very small cross section fixation members or haptics extending outwardly to create an overall size, between the free ends of the haptics, in the range of about 9 mm to about 14 mm. Any forces exerted on the haptics, for example, during installation or implantation of the IOL, or during use of the IOL, create high stress at the junction between the haptics and the optic. It is thus advantageous that the fixation member or members have high tensile strength, flexibility and fatigue resistance.

The items, for example, cores, buttons and the like, employed in accordance with the present invention comprise materials selected from methyl methacrylate homopolyers, co-polymers of methyl methacrylate and one or more other monomers, such as butyl acrylate, ethyl acrylate, lauryl acrylate and the like. In addition, the presently useful methyl methacrylate-containing copolymers can include polymerizable ultraviolet (UV) light absorbers, for example, present in the range of about 0.01% to about 2% by weight of the copolymer, effective to provide the desired degree of UV absorbance to the final IOL product. Examples of such UV absorbing monomers include functionalized benzophenones, functionalized benzotriazoles and the like. The presently useful items may include an effective amount of one or more other components to provide or enhance one or more properties which are beneficial in making the IOL and/or in the final IOL itself. For example, a UV absorbing additive (not polymerized) may be included or physically mixed into the item.

The methyl methacrylate homopolymers and/or methyl methacrylate-containing copolymers preferably comprise a major amount, i.e., at least about 50% by weight, and more preferably at least about 80% or about 90% by weight, of the item to be processed in accordance with the present invention. The optic of the final IOLs, and preferably the compressed items, are optically clear.

In order to provide a blank from which an IOL is to be formed in accordance with the present invention, an item, for example, a core, of uncompressed material is provided. This item, while it is uncompressed, includes a polymeric material which is fully polymerized. Thus, the processing, e.g., compressing, in accordance with the present invention, preferably results in substantially no additional polymerization or curing of this polymeric material.

Any suitable system and equipment may be employed to provide the compressed items and form IOLs from such compressed items in accordance with the present invention. Thus, the specific system and equipment employed is not critical and, for example, may be selected from systems and equipment which are conventionally employed to compress PMMA-type materials and to form IOLs from PMMA-type materials. The systems and equipment described herein are illustrative of the systems and equipment which may be employed.

In accordance with one embodiment, the uncompressed core, which is transparent and colorless and is made of, for example, PMMA, is placed on the platen of a press or similar device suitable for applying a compressive force to the core between two heating plates so that the thickness of the core is located between the plates and separates the plates. The heating plates are energized so as to heat the core to a temperature above about 30° C., preferably between about 80° C. to about 130° C. and more preferably between about 80° to about 125° C. After the core is heated to the desired temperature, the heating plates are forced or urged toward each other, thereby subjecting the core to compression along an axis substantially parallel to the thickness of the core. This compression results is reducing the thickness of the core by 30% or less, preferably in the range of about 3% or about 5% to about 25% or 30%. After this compression, the compressed core is allowed to cool to below, for example, slightly below, the glass transition temperature of the core material before the force on the plates is released. Conveniently, the compressed core is cooled to room temperature, e.g., about 20° C. to about 25° C., before the force is released. The cooled, compressed core, which has an increased tensile strength relative to the uncompressed core, is now ready to be processed or formed into an IOL, such as IOL 10.

In one useful embodiment, only that portion or portions of the uncompressed material, for example, the uncompressed core, from which the haptic or haptics of the IOL are to be made are subjected to compression, as described herein. This can be accomplished by using heating plates designed to exert the desired compressive force on the outside ring of the core, while exerting little or no compressive force on the central region of the core, from which the optic of the IOL is formed. Preferably, the compressive force is applied so that the core expands outwardly away from the central region and not inwardly toward the central region. One advantage of this embodiment is that the tensile strength and/or other physical property or properties of the haptic or haptics of the IOL are enhanced while the optic of the IOL is affected, for example, distorted, to a reduced extent, if at all, by the compressive force.

The compressed core, which is thicker and larger in all dimensions than the IOL to be made therefrom, may be processed in accordance with conventional IOL forming techniques to produce an integral IOL, such as IOL 10. To illustrate, the compressed PMMA core can be formed into a bi-convex single piece IOL by a process including the following steps:

(1) making a posterior cut on the compressed core;
(2) milling the compressed core;
(3) making an anterior cut on the compressed core; and
(4) polishing and cleaning the processed core. The final IOL can be wrapped, for example, individually wrapped, and stored prior to being used.

It has been found that the controlled, limited compression employed in accordance with the present invention results in a compressed core which can be formed into an IOL, for example, using conventional IOL manufacturing techniques such as those described herein, at least as effectively and efficiently as forming an IOL from the uncompressed core using the same IOL manufacturing techniques.

The use of the material processed as described herein, provides IOLs with fixation members which have enhanced tensile strength, flexibility and fatigue resistance.

The following non-limiting examples illustrate certain aspects of the present invention.

EXAMPLES 1 TO 9

A series of compressed cores were prepared and tested for physical properties. Each of these compressed cores was made from a PMMA-containing material sold by ICI, Ltd. under the trademark Perspex® CQ-UV. Each of the uncompressed cores was 0.1 inch in thickness and had a diameter of about 0.7 inch.

Each of the cores was compressed as follows. The uncompressed core was placed between heating plates on the platen of a press. The core was situated so that the heating plates were separated by the thickness of the uncompressed core. The heating plates were energized so as to heat the uncompressed core to the desired temperature. After this had occurred, the press was activated so as to apply a compressive force to the core and reduce the thickness by the desired amount. After this had occurred, and with the press still situated to apply force to the compressed core, the compressed core was cooled to room temperature. Afterwards, the compressed core was removed from the press and subjected to various stress/strain measurements at peak load and at ultimate stress.

Results of these tests are shown in Table I.

TABLE 1

|  | At Peak Load | | | At Ultimate Stress | | |
| --- | --- | --- | --- | --- | --- | --- |
|  | Load, lb. | Stress, lb/in² | Strain % | Load, lb. | Stress, lb/in² | Strain % |
| Control | 36.5 | 10,418 | 6.0 | 18.2 | 5,175 | 6.1 |
| 80° C. (.010)[1] | 31.0 | 10,055 | 6.0 | 13.9 | 4,500 | 6.1 |
| 80° C. (.020)[1] | 29.8 | 11,790 | 6.3 | 19.8 | 7,853 | 6.6 |
| 105° C. (.030)[1] | 38.2 | 11,863 | 7.4 | 19.9 | 6,171 | 7.5 |
| 105° C. (.010)[1] | 40.4 | 12,525 | 9.3 | 25.1 | 7,792 | 40.6 |
| 105° C. (.020)[1] | 35.1 | 10,882 | 7.0 | 14.3 | 4,429 | 18.3 |
| 105° C. (.030)[1] | 34.7 | 10,761 | 6.1 | 16.2 | 5,019 | 6.1 |
| 120° C. (.010)[1] | 46.9 | 13,406 | 10.2 | 23.0 | 6,574 | 41.4 |
| 120° C. (.020)[1] | 41.2 | 12,780 | 8.6 | 25.9 | 8,049 | 19.3 |
| 120° C. (.030)[1] | 41.5 | 11,843 | 8.5 | 21.4 | 6,097 | 17.4 |

[1]This number represents the amount of inches that the thickness of the original core was reduced.

These results indicate that the compressed cores tested generally have enhanced tensile strength and enhanced resistance to stress and strain relative to the uncompressed (Control) core. A relatively small number of the compressed cores tested exhibit no such enhancements. The results presented in Table 1 are based on a single core tested at each set of conditions. This, together with the inherent variability of the test procedure employed, are considered to be the two major reasons for certain of the compressed cores exhibiting no property enhancements. Under more controlled or less variable conditions, significantly enhanced tensile strength and resistance to stress and strain, relative to uncompressed cores, should occur throughout the range of test conditions noted in Table 1.

EXAMPLE 10

A number of cores having compositions similar to those described in Example 1, were compressed, as described in Example 1, at a temperature of 120° C. so as to reduce the thickness of the uncompressed core by 10%. These compressed cores, along with a number of uncompressed cores, were conventionally formed into intraocular lenses, similar in configuration to IOL 10, as shown in the drawings.

These lenses were subjected to a reverse bending test to determine the strength of the haptics of such IOLs.

The results of these reverse bending tests indicated that the haptics of the IOLs made from the compressed cores broke on the average upon the application of a force equal to 164 g. The haptics of the IOLs made from the uncompressed cores broke on the average upon the application of a force equal to 12 g. This substantial improvement in haptic bending strength, more than 1250% improvement, is clear evidence that the present controlled and limited compression processing results in IOLs having very beneficial physical properties, such as tensile strength and flexibility, which are very much enhanced as a result of this compression processing.

While this invention has been described with respect to various specific examples and embodiments, it is to be understood that the invention is not limited thereto and that it can be variously practiced within the scope of the following claims.

What is claimed is:

1. A method of making an intraocular lens comprising:
    compressing a core having a thickness to reduce said thickness in a range of 3% to 25% and form a compressed lens blank having a compressed thickness and a size so that only a single intraocular lens is formed therefrom, said core comprising a polymer selected from the group consisting of methyl methacrylate homopolymers, methyl methacrylate-containing copolymers and mixtures thereof, provided that said compressed lens blank has increased tensile strength relative to said core; and
    forming a single intraocular lens including an optic and at least one fixation member secured to said optic and extending from said optic from said compressed lens blank.

2. The method of claim 1 wherein said compressing reduces said thickness in a range of 5% to 25%.

3. The method of claim 1 wherein said compressing occurs along an axis substantially parallel to said thickness and at a temperature in the range of about 80° C. to about 130° C.

4. The method of claim 1 wherein said forming includes machining said compressed lens blank and said compressing occurs at conditions such that said machining is substantially no more difficult relative to substantially identically machining said core which is not subjected to said compressing.

5. The method of claim 1 wherein said compressing occurs at a temperature in the range of about 80° C. to about 130° C.

6. The method of claim 1 wherein said at least one fixation member has a reverse bend strength which is increased by about 1250% or more relative to a fixation member formed from an identical core which is not subjected to said compressing.

7. The method of claim 1 wherein said at least one fixation member has a reverse bend strength of at least about 164 g.

8. The method of claim 1 wherein said compressing occurs along an axis substantially parallel to said thickness.

9. A method of making an intraocular lens comprising:
    compressing a core having a thickness along an axis substantially parallel to said thickness to reduce said thickness and form a compressed lens blank having a compressed thickness and a size so that only a single intraocular lens is made therefrom, said core comprising a polymer selected from the group consisting of methyl methacrylate homopolymers, methyl methacrylate-containing copolymers and mixtures thereof, provided that said compressed lens blank has increased tensile strength relative to said core; and
    forming a single intraocular lens including an optic and at least one fixation member secured to said optic and extending from said optic from said compressed lens blank, said at least one fixation member having a reverse bend strength which is increased by about 1250% or more relative to a fixation member formed from an identical core which is not subjected to said compressing.

10. The method of claim 9 wherein said compressing reduces said thickness in a range of 5% to 25%.

11. The method of claim 9 wherein said forming includes machining said compressed lens blank and said compressing occurs at conditions such that said machining is substantially no more difficult relative to substantially identically machining said core which is not subjected to said compressing.

12. The method of claim 9 wherein said compressing occurs at a temperature in the range of about 80° C. to about 130° C.

13. The method of claim 9 wherein said at least one fixation member has a reverse bend strength of at least about 164 g.

14. A method of making an intraocular lens comprising:

compressing a core having a thickness along an axis substantially parallel to said thickness to reduce said thickness and form a compressed lens blank having a compressed thickness and a size so that only a single intraocular lens is made therefrom, said core comprising a polymer selected from the group consisting of methyl methacrylate homopolymers, methyl methacrylate-containing copolymers and mixtures thereof, provided that said compressed lens blank has increased tensile strength relative to said core; and forming a single intraocular lens including an optic and at least one fixation member secured to said optic and extending from said optic from said compressed lens blank, said at least one fixation member having a reverse bend strength of at least about 164 g.

15. The method of claim 14 wherein said compressing reduces said thickness in a range of 5% to 25%.

16. The method of claim 14 wherein said forming includes machining said compressed lens blank and said compressing occurs at conditions such that said machining is substantially no more difficult relative to substantially identically machining said core which is not subjected to said compressing.

17. The method of claim 14 wherein said compressing occurs at a temperature in the range of about 80° C. to about 130° C.

18. The method of claim 14 which further comprises forming said optic from said compressed lens blank by machining.

* * * * *